United States Patent [19]

Swinger et al.

[11] Patent Number: 4,660,556

[45] Date of Patent: Apr. 28, 1987

[54] METHOD AND APPARATUS FOR MODIFYING CORNEAL BUTTONS

[75] Inventors: Casimir Swinger, New York, N.Y.; Daniel Cassiday, Jersey City, N.J.

[73] Assignee: Techno Opthalmics International, Inc., Irvine, Calif.

[21] Appl. No.: 701,558

[22] Filed: Feb. 14, 1985

[51] Int. Cl.[4] .............................................. A61B 17/32
[52] U.S. Cl. .................................................... 128/305
[58] Field of Search ................ 128/305, 305.1, 303 R, 128/310

[56] References Cited

U.S. PATENT DOCUMENTS

| | | | |
|---|---|---|---|
| 3,058,471 | 10/1962 | Shope | 128/305 |
| 3,074,407 | 1/1963 | Moon et al. | 128/303 R |
| 3,129,971 | 4/1964 | Kobler | 128/303 R X |
| 3,139,298 | 6/1964 | Grabiel | 128/303 R X |
| 4,077,411 | 3/1978 | Ward | 128/305 X |
| 4,236,519 | 12/1980 | La Russa et al. | 128/305 |

Primary Examiner—Michael H. Thaler
Attorney, Agent, or Firm—J. Bradley Cohn

[57] ABSTRACT

Apparatus for altering the refraction of corneal tissue including a perforated die to deform the corneal tissue in a predetermined manner so that a cut in a transverse plane achieves the desired alteration. The corneal tissue is held firmly to the die both by suction and mechanical pressure. The method of so treating corneal tissue by deforming it to obtain a desired refraction with a planar cut including a method of holding the tissue in the deformed state by means of suction and mechanical pressure.

18 Claims, 14 Drawing Figures

METHOD AND APPARATUS FOR MODIFYING CORNEAL BUTTONS

BACKGROUND OF THE INVENTION

The present invention relates generally to an apparatus and method for modifying the shape and refractive power of the cornea, and more particularly, to removing a section of precise shape from a corneal button. (The term "corneal button" is used here and in the following description to refer to any disc-like or toroidal section of corneal tissue or other material such as soft contact lenses. It normally is lamellar and a partial thickness section of the cornea but need not be either).

The curvature of the anterior surface of the cornea, and thus its refractive power, may be modified by altering the shape of a corneal button and fixing the resultant to the cornea. One method to accomplish this, referred to as Keratomielusis, is to remove a lamellar (partial thickness) corneal disc from the patient's eye, machine out a section from the posterior surface using a specially adapted contact lenses lathe after freezing the corneal button, and returning it to the patient's eye. This approach has several drawbacks. The freezing can kill or damage the corneal tissue, and slows the patient's recovery. Further, freezing changes the thickness of the corneal button making accurate prediction of the final refractive correction difficult. Also, the machining operation, despite the freezing, is traumatic and can damage the corneal tissue. In addition, inaccuracies inherent in the lathe machining process (vibration, run-out, low surface cutting speed, etc.) limit the accuracy of the process. Furthermore, securing the corneal button in place by freezing is unreliable. Further, the modification is limited to relatively simple spherical shapes. Also, adjustment and operation of the apparatus is complicated and the procedure time-consuming.

There are three modifications of this procedure. In one, referred to as Homoplastic Keratomielusis, the corneal button is removed from the patient's eye as before, but now a donor corneal button is modified by the above procedure and sewn on the patient's eye. In another, referred to as Keratophakia, the corneal button is removed from the patient's eye as before, a donor corneal button modified by the above procedure, and the donor button inserted behind the patient's corneal button which is then sewn in place. In the third, referred to as Epikeratophakia, no corneal button is removed. Instead, a donor corneal button is prepared by the above procedure and sewn on over the patient's own cornea. All these methods employ the same freezing and lathe machining procedure, and thus suffer from all the same drawbacks cited above.

The prior art teaches the broad concept of deforming corneal tissue lens over a mold and altering its diopter by a planar cut as illustrated by Jose I. Barraquer, M.D. in the Arch. Soc. Amer. Oftal. Optom. (1967) 6-21 beginning particularly at page 54 through page 60. Barraquer teaches in this context the employment of the "congelation plate" to the microtome to freeze the tissue prior to cutting.

The Corning Glass Works of Corning, N.Y., have developed microporous glass for fixation of tissue by suction as taught at page 611 of a reprint from The Cornea, Work Congress, Washington; Butterworth's 1965, starting at page 605. The microporous glass is designed to create suction by capillary action and not by the application of the mechanically produced vacuum.

It is an object of this invention to provide an improved method of holding and distorting tissue during sectioning without the need of freezing or applying mechanical or chemical trauma to the tissue. The present invention permits immediate section of a corneal button for autoplastic surgery as well as homoplastic surgery without the time delay and trauma of mechanical or thermal (cryogenic) preservation.

The present invention circumvents these difficulties and is described below.

SUMMARY OF THE INVENTION

In accordance with the present invention, an apparatus is described that reshapes a corneal button by molding the corneal button over a die and cutting a lateral planar section from the molded corneal button. The shape of the die is chosen so as to produce the desired modification in shape of the corneal button resulting from a planar cut taken with the original corneal button molded over the die. Virtually any refractive correction can be obtained by proper selection of the die shape including myopic, hyperopic, and astigmatic corrections, as well as spherical aberation and other higher order corrections.

In a preferred embodiment of the invention, the corneal button is molded and secured to the die by a combination of a flexible membrane and a vacuum. The flexible membrane may have elastic or plastic qualities and is stretched over the corneal button biased toward the die, holding the button to the die. The die is porous (being constructed of a microporous material or having holes drilled through it) and a vacuum is drawn from the back side of the die causing both the corneal button and the flexible membrane to be molded and secured to the die face (even for concave die surfaces). The molding of the flexible membrane to the die face beyond the perimeter of the corneal button aids in securing the button to the die particularly the button edges. Alternate embodiments could employ a mechanical clamp in place of the flexible elastic membrane but the membrane is preferred.

Normally the anterior surface of the corneal button is placed against the die face, and this piece, rather than the excised piece, retained for use. Alternatively, the posterior surface of the corneal button could be placed against the die surface, or the excised piece retained for use, or both.

In a preferred embodiment, the die is seated on a pedestal which is mounted on a movable platform. The pedestal has a guide for a slip-on ring that holds the flexible membrane. The guide insures that the membrane is pressed over the corneal button with proper tension and minimum disturbance to the button. The cutting blade with motor is attached to a fixed platform so aligned to allow the movable base to move the corneal button transverse its axis and horizontally across the cutting blade edge, producing the lateral planar cut. This horizontal motion is controlled by a motorized translator to produce a smooth steady cut. Vertical height of the movable base can be adjusted with a manual micrometer translator to control cut thickness. During the cutting operation, both the corneal button and the flexible membrane are cut. Alternatively, the membrane could have a central aperture so it would not be cut during the cutting operation. Cutting may be done with circular or reciprocating blades or other known cutting means such as laser rays and the like.

In a preferred embodiment, the planar cut is done with a rotating thin circular blade sharpened with a single bevel. The blade is attached to a motor using a precision arbor to minimize run-out during blade rotation. To reduce friction and vibration between the blade's lower face and the corneal button, the plane of rotation of the blade is tilted slightly toward the cutting plane but not so much as to cause significant deviation from a planar cut. (The tilt could be increased and adjusted to allow for astigmatic correction using spherical dies). Friction and vibration between the blade's upper surface and the corneal material being excised is reduced by a fixed platform riding between the blade and excised material. This platform also serves to stabilize the cutting blade, and set a better angle between work and cutting blade.

An object of this invention is to provide a new and improved method and apparatus for modifying the shape of a corneal button in a precise, reliable, and predictable manner.

Another object of this invention is to provide a means for fixing and molding a corneal button to the surface of a die, the die being of pre-selected shape (including convex, concave, toric, and compound surfaces), without freezing or otherwise traumatizing the corneal button.

A still further object of this invention is to provide a means of accurately making a lateral planar cut from a molded corneal button without damaging either the button or the excised material.

It is an object of the invention to provide a means of reshaping a corneal button by molding over a die so a desired optical result may be obtained by a single planar cut to reduce the damage and trauma to the tissue. It is an object of the invention to perform the foregoing in a new manner as well as by a new means.

Still another object of this invention is to provide a means of automatically advancing the molded corneal button across the cutting blade, and a means to accurately adjust the thickness of the cut.

Still another object of this invention is to provide an instrument that is simple and safe to use, and one that minimizes the time that the corneal button is on the instrument.

Other objects of this invention will in part become apparent in the following description.

DESCRIPTION OF THE PREFERRED EMBODIMENTS

Figure 1:
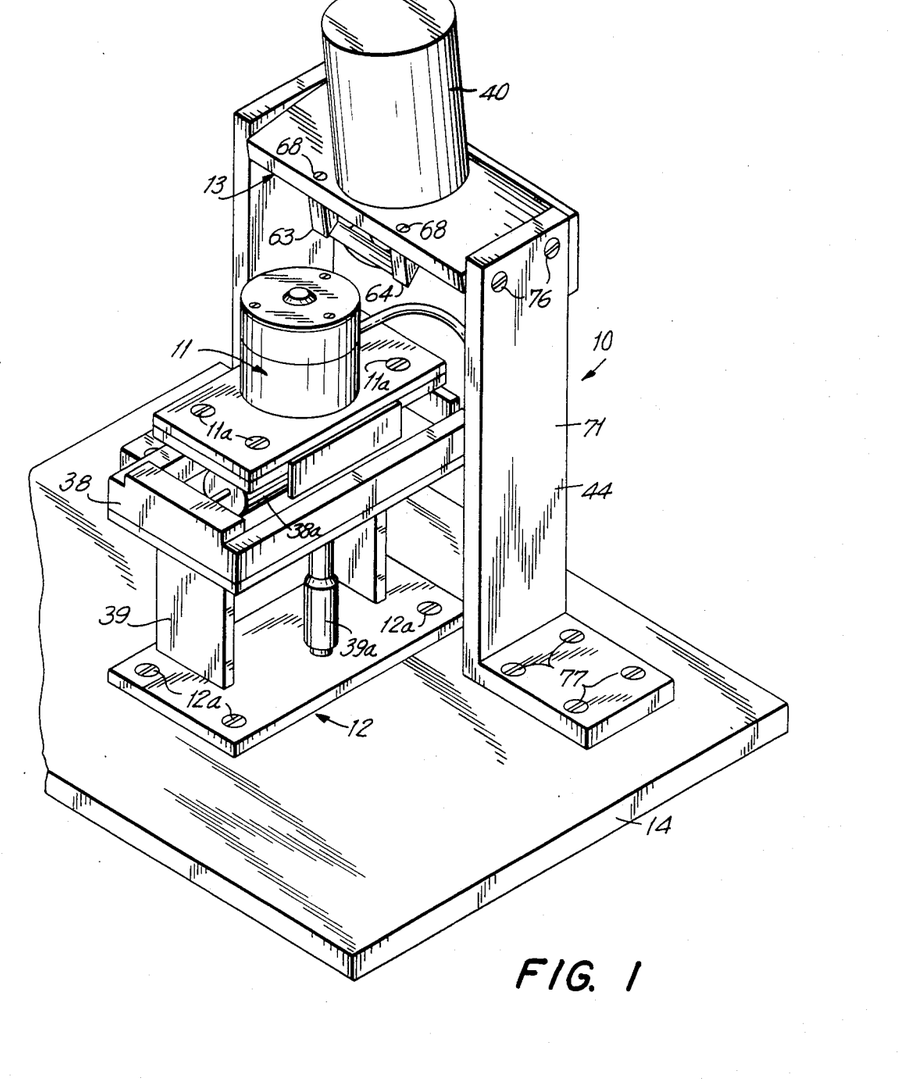
FIG. 1 is a perspective view of an instrument embodying the invention.

Referring now to FIG. 1 of the drawings, 10 designates an instrument embodying the invention and comprised generally of a fixation assembly 11, translator assembly 12, a cutting assembly 13, and a base plate 14.

Figure 2:
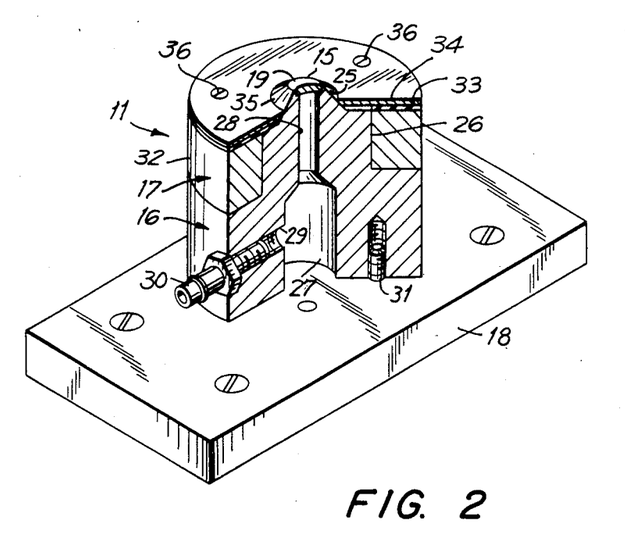
FIG. 2 is a perspective view of the fixation assembly with parts broken away and in cross-section.

Fixation assembly 11, as shown in FIG. 2, has a shaping die 15, a pedestal 16, a fixation collar 17, and a base 18.

Shaping die 15 is a cylindrical disc made of microporous glass with the top face 19 shaped to provide the desired modification in shape of a corneal disc resulting from a planar cut in a plane transverse the axis of the corneal disc 20 when disc 20 is molded and secured over the shaping die. Die 15 can be any desired shape including spherical and toric convex 21, FIG. 2b and concave 21a, FIG. 2c. Microporous material is used to allow a vacuum to be drawn through it to mold and help secure the corneal disc to the shaping die during the cutting operation. Alternatively, small holes 22 could be drilled through a non-porous shaping die 23.

Figure 2A:
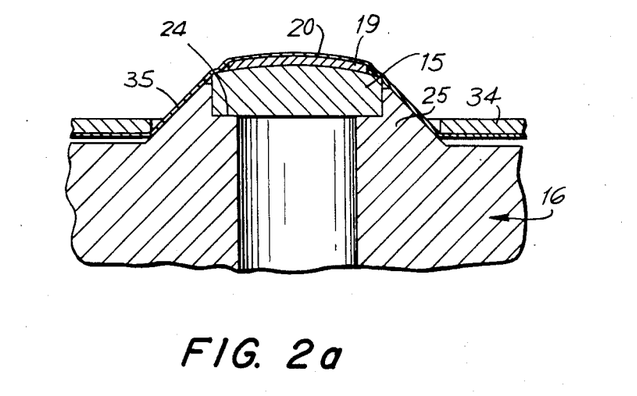
FIG. 2a is an enlarged sectional elevation of part of the fixation assembly.
Figure 2B:
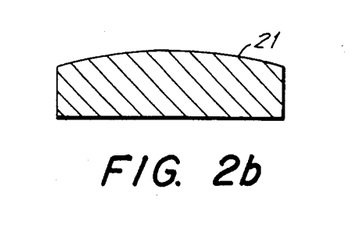
FIG. 2b is an enlarged sectional side view of a convex die.
Figure 2C:
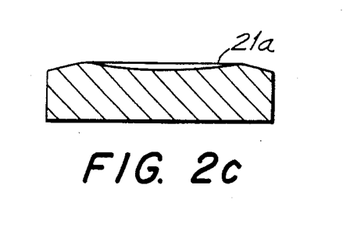
FIG. 2c is an enlarged sectional side view of a concave die.
Figure 2D:
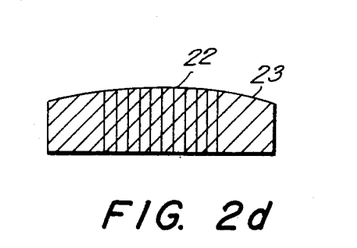
FIG. 2d is an enlarged sectional side view of a modified construction for the shaping die.
Figure 2E:
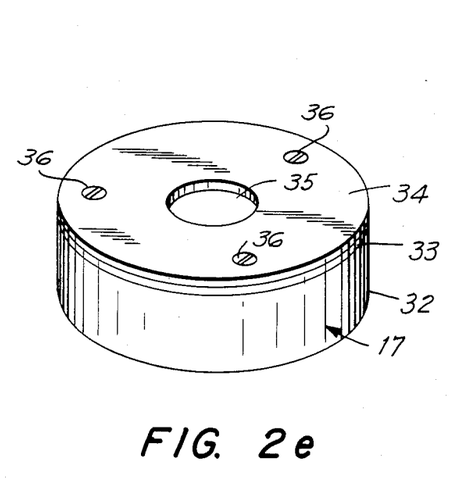
FIG. 2e is an enlarged perspective view of the fixation collar.

Referring to FIGS. 2 and 2a, an annular recess 24 at the top of a cone-shaped extension 25 of pedestal 16 forms a seat for shaping die 15. Pedestal 16 is cylindrical with an annular recess 26 formed to accept fixation collar 17. A cylindrical vacuum chamber 27 formed inside pedestal 16 communicates with a reduced bore 28 which in turn is in communication with porous die 15 in die seat 24. The chamber is evacuated through a threaded bore 29 drilled and tapped from the surface of the pedestal 16. A standard vacuum line fitting 30 is screwed into threaded bore 29. Pedestal 16 is secured to the fixation assembly base 18 by a plurality of screws 31, one of which is shown in FIG. 2.

Fixation collar 17 consists of an annular alignment ring 32, a sealing washer 33, a retaining washer 34, and a flexible membrane 35. Membrane 35 may be of any suitable material such as Saran ® plastic wrap, Reynolds ® plastic wrap, Dental Dam TM rubber sheeting, and Parafilm TM sheeting. It may be desirably be elastic in character to apply force on button or disc 30 more uniformly throughout the area of contact. Alignment ring 32 is designed to slip snuggly over annual recess 26 of pedestal 16. Flexible membrane 35 is a circular sheet of thin elastic material. Retaining ring 34 is a thin metal (or plastic) washer, and sealing washer 33 is rubber or other resilient material. Retaining washer 34, elastic membrane 35 and alignment ring 32 are sandwiched together (in that order) and secured by screws 36 threaded into pedestal 16.

A desired shaping die 15 is seated in recess 24 and a corneal disc 20 is placed over die 15. Fixation collar 17 is slipped onto recess 26˙ so that membrane 35 is stretched over corneal disc 30 pressing it and its edges against face 19 of die 15. Fixation assembly 11 is mounted on and secured to the translator assembly 12 by screws 11a. Assembly 12 is secured by screws 12a to base plate 14.

Translator assembly 12, FIG. 1, consists of a commercially available motorized horizontal axis translator stage 38 mounted on a standard manually operated vertical axis translator stage 39. The vertical axis translator is used to adjust the thickness of the cut by means of micrometer 39a while the horizontal translator moves the corneal disc through the cutting blade producing the cut. The motor 38a insures a smooth and even cut.

Figure 3:
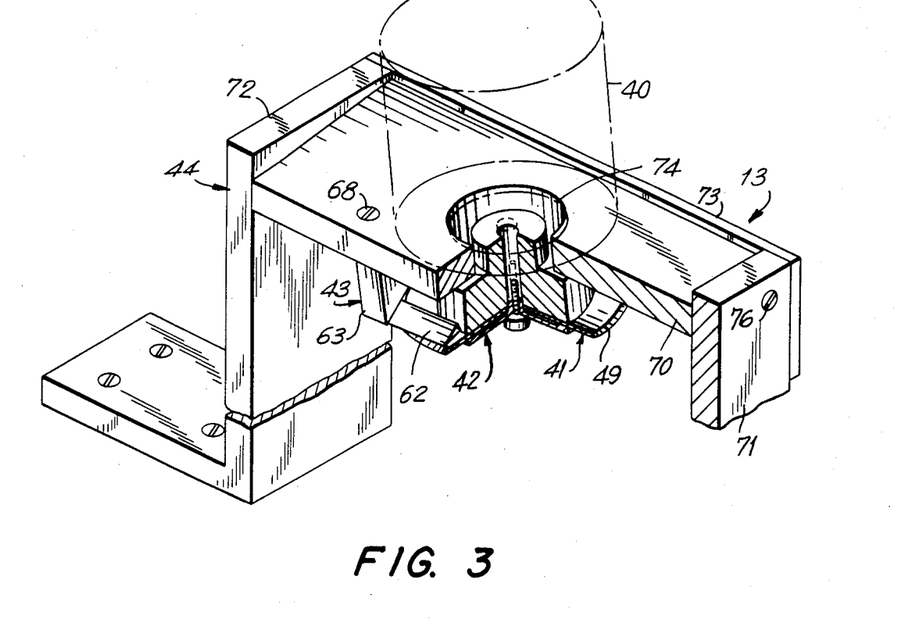
FIG. 3 is a perspective view of the cutting assembly with parts broken away and in cross-section.
Figure 3A:
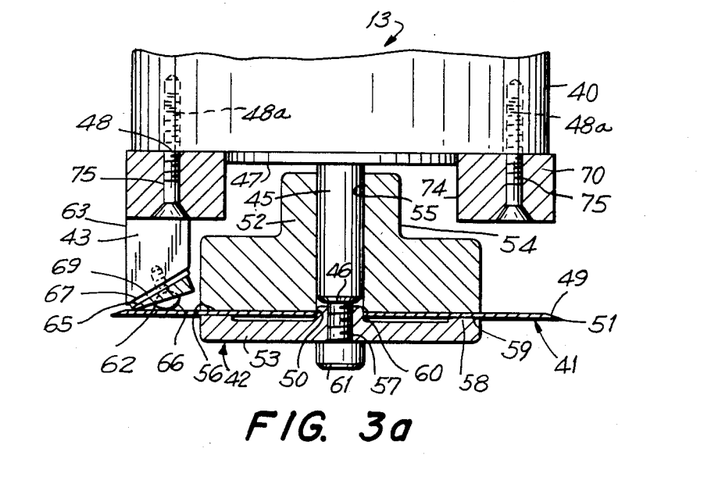
FIG. 3a is an enlarged sectional side elevation of part of the cutting assembly.

Cutting assembly 13, FIGS. 1, 3 and 3a, has an electric motor 40, a cutting blade 41, an arbor 42, a material platform 43, and a mounting platform 44. The motor 40 is a standard fractional horsepower precision permanent magnet D.C. motor. The motor shaft 45 is precision ground with a centered tapped hole 46 in its end. Motor 40 has a circular mounting flange 47 and tapped mounting holes 48a on its front face 48.

The cutting blade 41 is a thin flat circular sheet of stainless steel (or similar material) with a sharpened edge created by a single bevel 49 on its upper face. Cutting blade 41 has a center hole 50 which is accurately centered with the circumference of the blade cutting edge 51.

The arbor 42, FIGS. 3 and 3a, consists of a faceplate 52 and a securing plate 53. Faceplate 52 is cylindrical with an annular reduced cylindrical boss 54 and a central bore 55. The bottom face of the cylinder 56 is ground flat in a plane normal to bore 55. The faceplate is press fitted onto motor shaft 45. The securing plate 53 is a cylindrical disc with a circular hole 57 through its center. The securing plate has an annular extension 58 on the outer perimeter of its upper face 59, and a cylindrical extension 60 along the center of the securing plate. The O.D. of cylindrical extension 60 closely matches the I.D.'s of the cutting blade hole 50 and the arbor faceplate bore 55. The cutting blade 41 is pressed on over extension 50 with the beveled edge 49 facing away from plate 53. The blade and securing plate are attached to the faceplate 52 by a bolt 61. The extension 60 extends into the bore 55 accurately centering blade 51 on the axis of rotation of shaft 45.

Material platform 43, FIGS. 1, 3 and 3a, consists of a thin bar 62 with triangular cross section supported by two rectangular arms 63 and 64. The thinner edge 65 of bar 62 is positioned to lie against the upper surface of cutting blade 41 just behind its cutting edge to stabilize the blade during rotation and prevent deflection during the cutting operation. Further, the platform bar 62 reduces friction and vibration on the corneal button that would occur if the button contacted the upper surface of cutting blade 41 and also holds the excised material at an angle to the cutting plane to improve cutting efficiency and accuracy. Support bar 62 is secured to the rectangular arms 63 and 64 with screws 66. The end 67 of the rectangular arms is cut at an angle to give the support bar the desired inclination to the cutting plane. The rectangular arms are attached to motor support bar 70 with screws 68. Shims 69 are used to adjust the support bar to lie against the cutting blade.

A mounting platform for motor 40 comprises a motor support bar 70, two support arms 71 and 72 and a protection and stabilizing plate 73. Motor support bar 70 is rectangular with a pilot bore 72 to accept the motor mounting flange 47. The motor 40 is secured to support bar 70 with screws 75. Motor support bar 70 is connected to the vertical sides of the two "L" shaped support arms 71 an 72 with screws 76 at an angle slightly inclined to the horizontal so that the cutting blade is inclined to the cutting plane to reduce friction and vibration on the corneal button during the cutting operation. Support arms 71, 72 are attached to the instrument base 14 with screws 77. Protection plate 73 is attached to the back of support arms 71, 72 creating a housing for the cutting blade for protective purposes and increasing the stability of the support arms 71, 72.

A second embodiment of the invention employs a reciprocating rather than rotating cutting blade. The instrument 10 is the same as described above except that the cutting assembly 13 is replaced by the modified cutting assembly shown in FIG. 4. The modified cutting assembly consists of a microkeratome 79, a pair of gripping arms 80 and 81, a pair of support blocks 82 and 83, and a pair of support columns 84 and 85. The microkeratome 79 is a commercially available instrument made by Steinway Instrument Company of San Diego, Calif. that employs a reciprocating blade 88a for sectioning of corneal tissue. The microkeratome is held securely in position by gripping arms 80 and 81. The gripping arms 80, rectangular bars each with a horizontal key 86 running the length of its gripping face 86a. The key mates with the guide grove 87 in the microkeratome and is used to provide proper alignment of the microkeratome. Also in the gripping face of each of gripping arms 80, 81 is a vertical slot 88 to provide clearance for the microkeratome blade 88a as it oscillates. Each gripping arm also has a longitudinal slot 89 to slidingly receive a locking screw 93.

Figure 4:
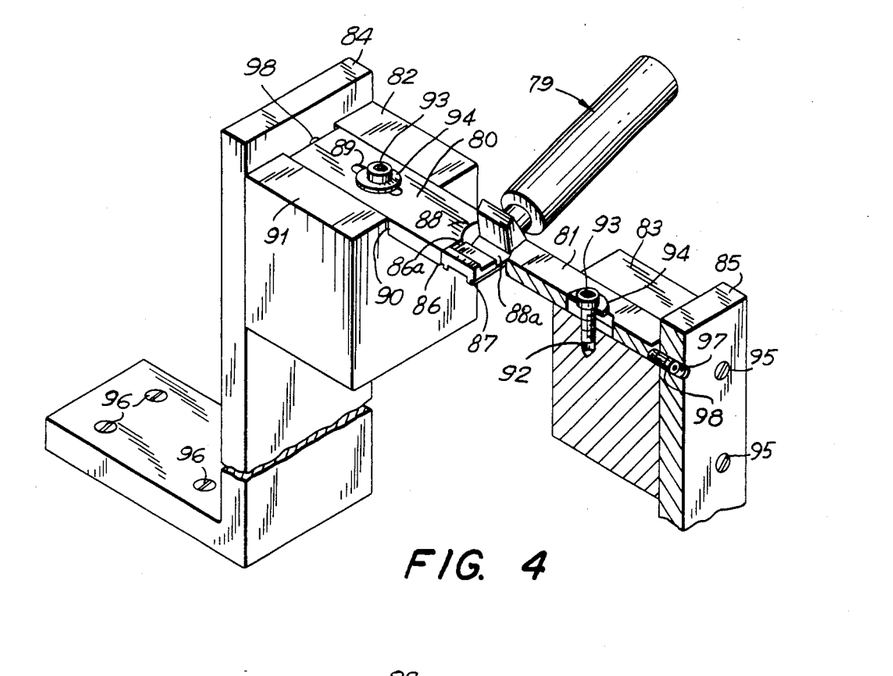
FIG. 4 is a perspective view of a modified construction for the cutting assembly.

Each support block 82, 83 is rectangular with a longitudinal channel 90 in its upper face 91 to slidingly receive gripping arm 80, 81. Channel 90 has a threaded hole 92 aligned with the slot 89 in each gripping arm 80, 81. Gripping arms 80, 81 are secured to the support block by a screw 93 and washer 94. The support blocks are attached to the support columns 84 and 85 by screws 95. Support columns 84, 85 are "L" shaped and attached to instrument base 14 with screws 96. Each support column has a tapped hole 97 for a set screw 98 that aligns with channel 90 in support block 82.

Microkeratome 79 is secured in position between gripping arms 80, 81 with guide 87 in key 86. The set screws 98 are tightened to clamp microkeritome 79 in proper position, and then screws 93 tightened to lock gripping arms 80, 81 in place.

Figure 5:
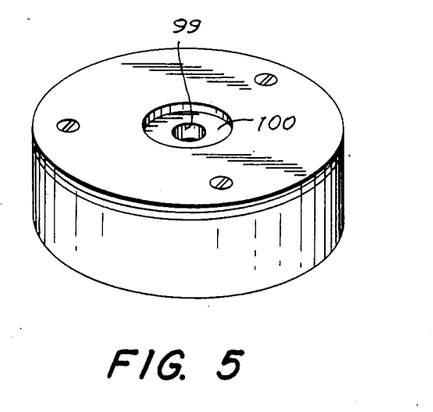
FIG. 5 is an enlarged perspective view of modified construction for the fixation collar.

In another embodiment of the invention, the need to cut through the elastic membrane during the cutting operation is avoided. The fixation collar 17 is the same as in the preferred embodiment except that there is a circular hole 99, FIG. 5, in the center of flexible membrane 100. The size of this hole is chosen so that the elastic membrane is not cut during the cutting operation but the membrane still secures corneal disc and its edge to the shaping die.

Figure 6:
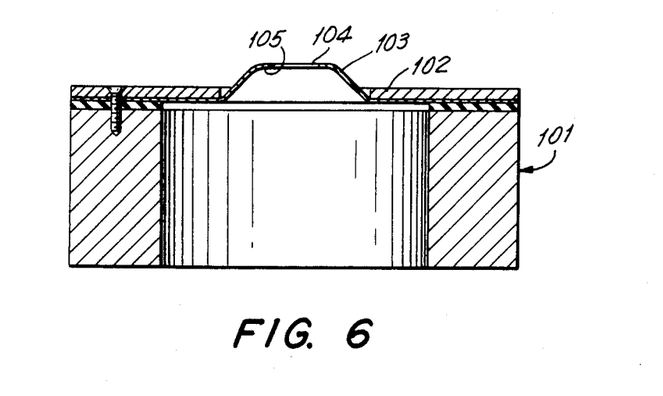
FIG. 6 is an enlarged sectional elevation of another modified construction for the fixation collar.

In still another embodiment of the invention, the corneal disc is secured by a flexible ring rather than the elastic membrane. The fixation collar 101, FIG. 6, is the same as in the preferred embodiment except that the flexible membrane is replaced by a thin plastic (or metal) sheet 102 with a dome shaped extrusion 103 in its center and extending upward as shown in FIG. 6. The extrusion 102 has a hole 104 in the center. When the fixation collar 101 is slipped over the pedestal 16 the corneal disc 20 protrudes through the hole 104 with the extrusion edge 105 contacting the corneal button perimeter and pressing it on the shaping die 15.

Figure 7:
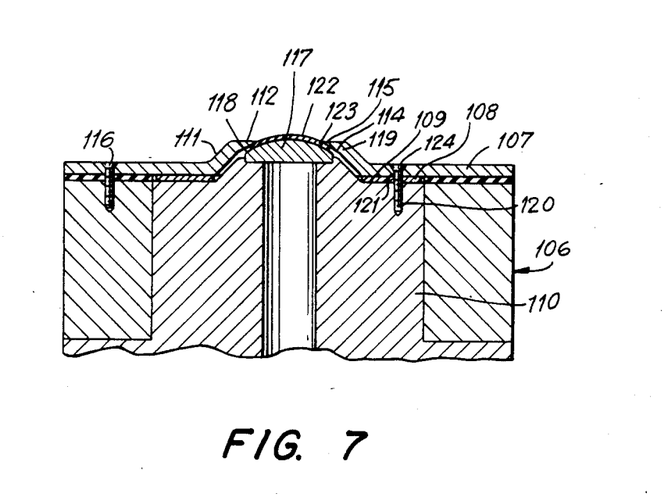
FIG. 7 is an enlarged sectional elevation of part of the fixation assembly illustrating a modified construction for the fixation collar.

In still yet another embodiment of the invention, the corneal disc is secured by a rigid ring rather than the flexible membrane. The fixation collar 106, FIG. 7, is the same as in the preferred embodiment except that the flexible membrane 35 and retaining ring 36 are replaced by a rigid clamping ring 107 and a spacer ring 108. The spacer ring 108 is a flat metal ring and is placed on the flat shoulder 109 of the pedestal 110. The clamping ring 107 is a thin circular plate of metal with a cone shaped extrusion 111. The top face 112 of this extrusion 111 is flat and has a hole 113 in the center. The undersurface 114 tapers away from the hole edge 115. The clamping ring 107 is secured to the fixation collar with screws 116. The shaping die 117 is the same as die 15 in the preferred embodiment except for a bevel 118 extending around the perimeter 119 of the die 117. The pedestal 110 is the same as in the preferred embodiment except for tapped holes 120. Both the spacer ring 108 and the clamping ring 107 have holes 121 aligned with holes 120. To secure the corneal button 122, the fixation collar 106 is slid down over the pedestal 110. The edge 115 contacts the corneal button perimeter 123 pressing the corneal button 122 to the shaping die 117. The fixation collar 106 is secured to the pedestal 110 with screws 124. The spacer ring 108 is selected to yield the desired pressure on the corneal button perimeter 123 by the edge 115.

Figure 8:
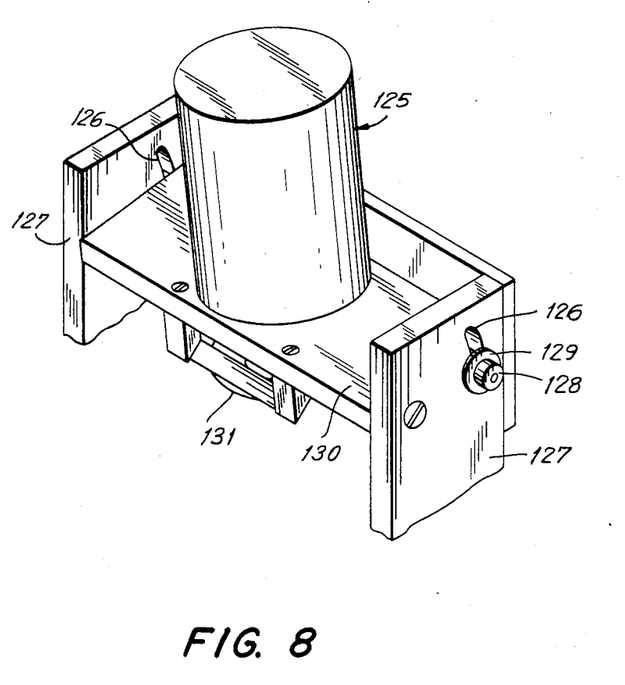
FIG. 8 is a perspective view with parts broken away of a modified construction for a cutting assembly.

In another embodiment of the invention the angle between the plane of rotation of the blade and the cutting plane is made adjustable. As this angle is increased, the cut becomes increasingly more cylindrical (deviating from planar) thereby creating a torque type correction on a corneal button molded over a spherical die. This type of correction is useful for astigmatic correction. The modified cutting assembly 125 is shown in FIG. 8. The cutting assembly 125 is the same as in the preferred embodiment except arc-shaped slots 126 are cut in the support arms 127 through which locking bolts 128 with washers 129 are screwed in the motor support bar 130. The cutting blade 131 is adjusted to the desired angle and secured by tightening bolts 128.

What is claimed is:

1. Apparatus for altering the refractive power of a corneal button comprising a preformed die constructed and arranged to distort a corneal button held firmly in contact with the surface of said die, a vacuum source, said die having pores formed therethrough, said pores communicating with said surface and said vacuum source, a flexible membrane, means to apply said membrane across a corneal button supported on said die to press said button in conjunction with said suction toward said surface, cutting means and reciprocating support means supporting one of said cutting means and said die with its associated membrane and vacuum source for transverse movement with respect to the other and in spaced relation thereto whereby said corneal button is firmly but gently distorted on the face of said die, severed by a transverse planar cut to provide a different optical refractive power when removed from said apparatus.

2. Apparatus as set forth in claim 1 wherein the surface of said die is convex.

3. Apparatus as set forth in claim 1 wherein the surface of said die is concave.

4. Apparatus as set forth in claim 1 wherein the surface of said die is astigmatic.

5. Apparatus as set forth in claim 1 wherein said membrane has a central aperture formed therein and adapted to be centered over said corneal button whereby said membrane engages a circumferential portion of said button to press it toward said die and said planar cut is made in the area underlying said membrane aperture only.

6. Apparatus for altering the refractive power of a corneal button comprising means for distorting a corneal button, said means including a preformed die constructed and arranged to distort a corneal button held firmly in contact with the surface of said die, a vacuum source, said die being in contact with said source and having pores communicating with said surface and said vacuum source, and a ring constructed and arranged to press a circumferential portion of said corneal button against said die to retain and gently distort said portion in firm contact therewith, cutting means and reciprocating means moving one of said cutting means and said die with its associate vacuum source and ring transverse each other and in spaced relation to perform a transverse planar cut through a corneal button held and molded to said die by said vacuum source and said ring.

7. Apparatus as set forth in claim 6 wherein said ring is flexible.

8. Apparatus in accordance with claims 1 or 6 wherein said cutting means comprises a rotary disc knife.

9. Apparatus as set forth in claims 1 or 6 wherein said cutting means comprises a reciprocating knife.

10. Apparatus in accordance with claims 1 or 6 constructed and arranged to support a plate adjacent said cutting means to receive the excised portion of said corneal button to reduce its contact with the said cutting means.

11. Apparatus in accordance with claims 1 or 6 constructed and arranged to support a plate in contact with said cutting means to stabilize said cutting means.

12. The method of modifying the refractive power of a corneal button in a manner obviating the need for a cryogenic step comprising gently supporting and distorting the shape of the button by pressing said button against a curved surface by simultaneously applying suction to the surface of the button in contact with the curved surface and substantially uniform mechanical pressure throughout the entire area not in contact with said surface including the edges of said button and then while said button is retained and gently distorted by said suction and said mechanical pressure against the curved surface severing in a plane substantially transverse to the axis of said button whereby thermal and mechanical trauma are substantially reduced.

13. The method set forth in claim 12 and further characterized in that the said uniform mechanical pressure results from drawing a flexible membrane to press said button including the edges thereof against said curved surface.

14. The method of modifying the refractive power of a corneal button in a manner obviating the need for a cryogenic step comprising gently supporting and distorting the shape of the button by pressing said button against a curved surface by simultaneously applying suction to the surface of the button in contact with the curved surface and applying substantially uniform mechanical pressure to the peripheral area not in contact with said surface and then while said button is retained and gently distorted by said suction and said mechanical pressure against the curved surface severing in a plane substantially transverse to the axis of said button whereby thermal and mechanical trauma are substantially reduced.

15. The method set forth in claim 14 and further characterized in that said uniform mechanical pressure results from drawing a flexible membrane to press said button including the edges thereof against said curved surface, said membrane having a central aperture of lesser diameter than the diameter of said button and said button is severed in the area not pressed by said membrane.

16. Apparatus for altering the refractive power of a corneal button comprising means for distorting a corneal button, said means including a preformed die constructed and arranged to distort a corneal button held firmly in contact with the surface of said die, a flexible membrane, and means to apply said membrane across a corneal button supported on said die to firmly press said button toward said surface, cutting means and reciprocating supporting means supporting one of said cutting means and said die with its associated membrane for transverse movement with respect to the other and in spaced relation thereto whereby said corneal button is firmly but gently distorted on the face of said die, severed by a transverse planar cut to provide a different optical refractive power when removed from said apparatus.

17. Apparatus for altering the refractive power of a corneal button comprising means for distorting a corneal button, said means including a preformed die constructed and arranged to distort a corneal button held firmly in contact with the surface of said die, and a ring located on the side of said corneal button opposite said die and constructed and arranged to press a circumferential portion of said corneal button against said die to firmly retain said portion in firm contact therewith, cutting means and reciprocating means moving one of said cutting means and said die with its associate ring transversely of each other and in spaced relation to perform a transverse planar cut on a corneal button held on said die by said ring.

18. Apparatus in accordance with claims 1 or 6 wherein said cutting means may be selectively tilted to produce an astigmatic cut substantially along said transverse plane.

* * * * *

UNITED STATES PATENT AND TRADEMARK OFFICE
CERTIFICATE OF CORRECTION

PATENT NO. : 4,660,556
DATED : April 28, 1987
INVENTOR(S) : Casimir Swinger and Daniel Cassiday It is certified that error appears in the above-identified patent and that said Letters Patent is hereby corrected as shown below:

Column 6, line 23, after "80", insert -- 81 are --.

Signed and Sealed this

Fifth Day of January, 1988

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,660,556

DATED : April 28, 1987

INVENTOR(S) : Casimir Swinger and Daniel Cassiday

It is certified that error appears in the above-identified patent and that said Letters Patent is hereby corrected as shown below:

Column 7, line 67, "claim 1" should read --claims 1 or 16--.

Column 6, line 23, after "80," insert --81 are--.

This certificate supersedes certificate of correction issued January 5, 1988.

Signed and Sealed this

Fourteenth Day of June, 1988

Attest:

DONALD J. QUIGG

*Attesting Officer*  *Commissioner of Patents and Trademarks*

Notice of Adverse Decision in Interference

In Interference No. 101,883, involving Patent No. 4,660,556, C. Swinger and D. Cassiday, METHOD AND APPARATUS FOR MODIFYING CORNEAL BUTTONS, final judgment adverse to the patentees was rendered April 19, 1989, as to claims 6, 8/6, 9/6, 10/6, 11/6, 12, 14 and 17.

*[Official Gazette September 19, 1989.]*

Disclaimer 4,660,556.—*Casimir Swinger*, New York, N. Y.; *Daniel Cassiday*, Jersey City, N.J. METHOD AND APPARATUS FOR MODIFYING CORNEAL BUTTONS. Patent dated Apr. 28, 1987. Disclaimer filed Sept. 29, 1989, by the inventors.

Hereby enters this disclaimer to claims 6, 8/6, 9/6, 10/6, 11/6, 12, 14, and 17 of said patent.
[ *Official Gazette December 5, 1989* ]